United States Patent
Tanabe et al.

(10) Patent No.: US 11,514,389 B2
(45) Date of Patent: Nov. 29, 2022

(54) SYSTEM AND METHOD FOR IPS CELL BANK USING INTERNET TECHNOLOGY

(71) Applicants: FANUC CORPORATION, Yamanashi (JP); I Peace, Inc., Los Altos, CA (US)

(72) Inventors: Koji Tanabe, Los Altos, CA (US); Kiyonori Inaba, Yamanashi (JP); Masaru Oda, Yamanashi (JP)

(73) Assignees: FANUC CORPORATION, Yamanashi (JP); I PEACE, INC., Los Altos, CA (US)

( * ) Notice: Subject to any disclaimer, the term of this patent is extended or adjusted under 35 U.S.C. 154(b) by 115 days.

(21) Appl. No.: 16/435,617

(22) Filed: Jun. 10, 2019

(65) Prior Publication Data

US 2019/0325381 A1 Oct. 24, 2019

Related U.S. Application Data

(63) Continuation of application No. 15/228,017, filed on Aug. 4, 2016, now Pat. No. 10,354,218.

(51) Int. Cl.
| | |
|---|---|
| G06Q 10/08 | (2012.01) |
| C12N 5/074 | (2010.01) |
| G06Q 30/06 | (2012.01) |
| G06Q 50/22 | (2018.01) |
| G06Q 10/06 | (2012.01) |

(52) U.S. Cl.
CPC ....... *G06Q 10/0832* (2013.01); *C12N 5/0696* (2013.01); *G06Q 10/087* (2013.01); *G06Q 10/06* (2013.01); *G06Q 30/06* (2013.01); *G06Q 50/22* (2013.01)

(58) Field of Classification Search
CPC ....... G06Q 10/087; G16H 40/20; G06F 19/00
USPC ......................................................... 705/2–3
See application file for complete search history.

(56) References Cited

U.S. PATENT DOCUMENTS

| | | | |
|---|---|---|---|
| 5,022,236 A | 6/1991 | Knippscheer et al. | |
| 5,325,678 A | 7/1994 | Borah et al. | |
| 5,985,653 A | 11/1999 | Armstrong et al. | |
| 6,226,997 B1 | 5/2001 | Vago | |

(Continued)

FOREIGN PATENT DOCUMENTS

| | | |
|---|---|---|
| CN | 102174395 A | 9/2011 |
| CN | 205794637 U | 12/2016 |

(Continued)

*Primary Examiner* — Robert W Morgan
*Assistant Examiner* — Rachel F Durnin
(74) *Attorney, Agent, or Firm* — Hauptman Ham, LLP

(57) ABSTRACT

A system for an iPS cell bank includes a terminal and a server. The terminal receives and sends a production request including a desired collection date of a somatic cell and a customer ID to the server. The server stores a collectable date for collecting the somatic cell, a producible period for producing an iPS cell, and a location and a stockable period for stocking the iPS cell; and determines: a collection date based on the desired collection date and the collectable date; a production period based on the collection date and the producible period; an acceptance date of the somatic cell based on the collection date and the production period; a stock location and a stock period based on the production period, the stockable location, and the stockable period; and a shipment date of the iPS cell based on the production period, the stockable location, and the stockable period.

7 Claims, 4 Drawing Sheets

(56) References Cited

U.S. PATENT DOCUMENTS

| | | | |
|---|---|---|---|
| 2005/0276792 A1* | 12/2005 | Kaminski | G16H 10/60 |
| | | | 435/372 |
| 2008/0215364 A1* | 9/2008 | Brevnova | G16H 40/67 |
| | | | 705/2 |
| 2010/0272694 A1 | 10/2010 | Yang et al. | |
| 2011/0054929 A1* | 3/2011 | Centeno | G06Q 30/08 |
| | | | 705/2 |
| 2011/0207209 A1 | 8/2011 | Hammons et al. | |
| 2013/0275236 A1 | 10/2013 | Koke et al. | |
| 2013/0325492 A1* | 12/2013 | Dudzinski | G16H 10/40 |
| | | | 705/2 |
| 2013/0345094 A1 | 12/2013 | Noggle et al. | |
| 2014/0278499 A1* | 9/2014 | Bowman | G06Q 30/0601 |
| | | | 705/2 |
| 2015/0203297 A1 | 7/2015 | Manning et al. | |
| 2015/0204598 A1 | 7/2015 | Affleck et al. | |
| 2015/0356500 A1 | 12/2015 | Larson et al. | |
| 2016/0114326 A1 | 4/2016 | Schryver | |
| 2016/0222355 A1* | 8/2016 | Noggle | C12N 5/0696 |
| 2016/0328521 A1* | 11/2016 | Mickles | G16H 10/60 |
| 2017/0299248 A1 | 10/2017 | High et al. | |
| 2017/0337337 A1* | 11/2017 | Heckerman | G16H 40/20 |

FOREIGN PATENT DOCUMENTS

| | | |
|---|---|---|
| JP | 2002027983 A | 1/2002 |
| JP | 2003108660 A | 4/2003 |
| JP | 2004119 A | 1/2004 |
| JP | 2004290134 A | 10/2004 |
| JP | 2004290140 A | 10/2004 |
| JP | 2004290147 A | 10/2004 |
| JP | 2005-112499 A | 4/2005 |
| JP | 2005285142 A | 10/2005 |
| JP | 20064299 A | 1/2006 |
| JP | 2008123 A | 1/2008 |
| JP | 2008-283972 A | 11/2008 |
| JP | 2011013752 A | 1/2011 |
| JP | 2012-243324 A | 12/2012 |
| JP | 2015502747 A | 1/2015 |
| JP | 2015100309 A | 6/2015 |
| JP | 2015130805 A | 7/2015 |
| JP | 2015-202918 A | 11/2015 |
| JP | 2015222539 A | 12/2015 |
| WO | 2010026656 A1 | 3/2010 |

* cited by examiner

FIG. 3

Table 101:

| ENTRY ID | ENTRY DATE | CUSTOMER ID | FIRST DESIRED COLLECTION DATE | SECOND DESIRED COLLECTION DATE | THIRD DESIRED COLLECTION DATE |
|---|---|---|---|---|---|
| 0001 | 2018/02/19 | 0102 | 2018/03/15 | 2018/03/16 | 2018/03/17 |
| 0002 | 2018/02/23 | 0023 | 2018/03/18 | 2018/03/19 | 2018/03/22 |
| 0003 | 2018/02/25 | 0085 | 2018/03/21 | 2018/03/22 | 2018/03/25 |
| ... | ... | ... | ... | ... | ... |

Table 102:

| ACCEPTANCE ID | COLLECTION INSTITUTION ID | COLLECTABLE DATE | ENTRY ID | BLOOD COLLECTION DATE | BLOOD ACCEPTANCE DATE |
|---|---|---|---|---|---|
| 0001 | 0001 | 2018/03/16 | 0001 | 2018/03/16 | 2018/03/17 |
| 0002 | 0002 | 2018/03/21 | 0003 | 2018/03/21 | 2018/03/22 |
| 0003 | 0003 | 2018/03/25 | | | |
| ... | ... | ... | ... | ... | ... |

Table 103:

| PRODUCTION ID | iPS CELL PRODUCIBLE PERIOD | ENTRY ID | iPS CELL PRODUCTION PERIOD | iPS CELL SHIPPING DATE |
|---|---|---|---|---|
| 0001 | 2018/03/16~2018/09/16 | 0001 | 2018/03/16~2018/09/16 | 2018/09/16 |
| 0002 | 2018/03/17~2018/09/17 | 0003 | 2018/03/17~2018/09/17 | CANCELED |
| ... | ... | ... | ... | ... |

Table 104:

| STOCK ID | STOCK SITE ID | STOCKABLE LOCATION | STOCKABLE PERIOD | ENTRY ID | STOCK LOCATION | STOCK PERIOD |
|---|---|---|---|---|---|---|
| 0001 | 0001 | TOKYO STOCK SITE | 2018/09/19~2068/09/19 | 0001 | TOKYO STOCK SITE | 2018/09/19~2068/09/19 |
| 0002 | 0002 | TOKYO STOCK SITE | 2018/09/20~2068/09/20 | 0003 | TOKYO STOCK SITE | ... |
| ... | ... | ... | ... | ... | ... | ... |

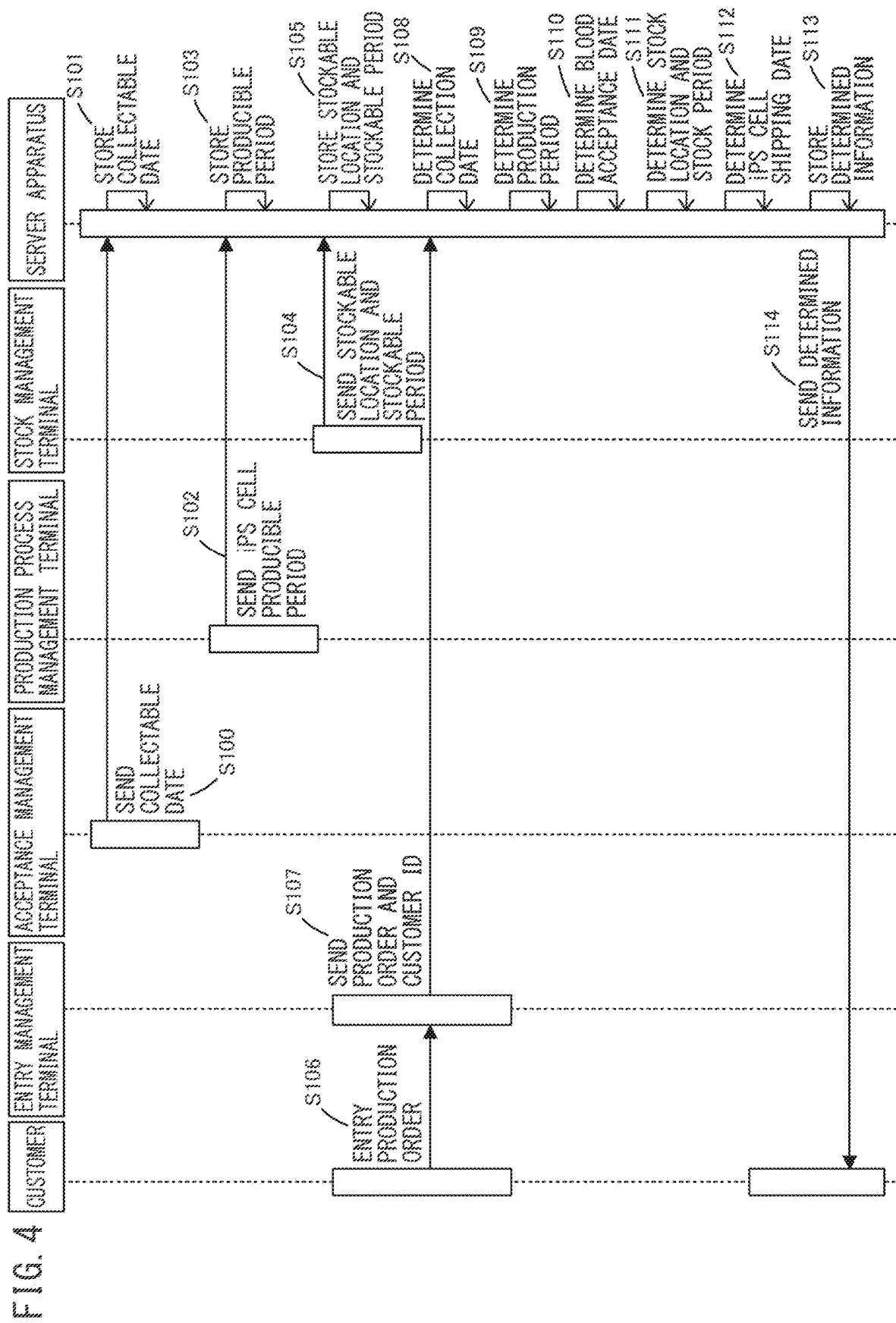

SYSTEM AND METHOD FOR IPS CELL BANK USING INTERNET TECHNOLOGY

RELATED APPLICATION

The present application is a continuation of U.S. application Ser. No. 15/228,017, filed Aug. 4, 2016. The disclosure of the above listed application is hereby incorporated by reference herein in its entirety.

BACKGROUND OF THE INVENTION

1. Field of the Invention

The present invention relates to a system and a method for an iPS cell bank using an Internet technology.

2. Description of the Related Art

In recent years, the iPS Cell Stock Project has progressed in regenerative medicine. In the iPS Cell Stock Project, blood is collected from healthy human leukocyte antigen (HLA) homozygous donors, and induced pluripotent stem cells (iPS cells) are generated and stocked in the Center for iPS Cell Research and Application, Kyoto University. In such a background, it is considered that business (system construction) in which regenerative medicine and clinical research are conducted using the stocked iPS cells is essential and urgently needed. In this respect, for example, literatures described below are known as the technologies of managing the inventory of medical supplies and the temperature of drugs.

Japanese Unexamined Patent Publication (Kokai) No. 2012-243324 describes the invention of a system for managing the inventory and order of expendable supplies (chemical samples and calibrators) used in a clinical analyzer for analyzing blood, tissue, and the like.

Japanese Unexamined Patent Publication (Kokai) No. 2005-112499 describes the invention of a management system for performing inventory management and ordering of expendable supplies (syringes, bandages, and rubbing alcohol) used in hospitals.

Japanese Unexamined Patent Publication (Kokai) No. 2015-202918 describes a system for performing temperature management of factories and repositories for commodities needing temperature management, such as foods and drugs, and for performing temperature management of the commodities during transporting the commodities.

SUMMARY OF THE INVENTION

The time, cost, and effort of production of iPS cells for clinical use are hurdles for practical use. This is because there is no management system capable of accurately performing the unified management of enormous data related to production management, quality management, and the like based on regulations as described.

There is concern that it is impossible to maintain and ensure the quality of iPS cells when appropriate management is not performed in a step of accepting somatic cells which are ingredients for producing the iPS cells, a step of producing the iPS cells, a step of stocking the iPS cells, and a step of transporting the iPS cells. Against the concern, it is preferable to perform analysis based on, for example, "Standard for Biological Ingredients" for ingredients used for producing regenerative medical products, "Ministerial Ordinance on Good Gene, Cellular and Tissue-based Products" (Ministerial Ordinance on GCTP) for production and quality management, Notifications from the Director of the Ministry of Health, Labour and Welfare "Guideline on Ensuring Quality and Safety of Drug Product, etc. Derived from Processing of Human (Autologous) iPS (-like) Cells" and "Guideline on Quality and Safety Assurance of Drug Product, etc. Derived from Human (Allogenic) iPS (-like) Cells", Q5A and Q5D agreed in the International Conference on Harmonisation (ICH) for generation of a cell bank and for a virus free test, and the like.

It is preferable to strictly evaluate the quality of generated iPS cells for clinical use. As a manner in the whole quality management of pharmaceutical products obtained by processing human iPS cells, and the like (including iPS cells which are ingredients), there is a regulation that the standard and testing method of iPS cells are set, and that the evidence thereof is provided. For example, the following quality evaluation items are demanded.

It is demanded to match various strict quality test management items such as:
  1) cell count and the number of surviving cells;
  2) identification test;
  3) test of purity of cells;
  4) process-related impurities testing;
  5) sterility testing and mycoplasma negative testing;
  6) endotoxin testing;
  7) viral test;
  8) characteristic test associated with iPS cells;
    (i) having pluripotency of being capable of differentiating into various somatic cells; and
    (ii) observing no gene mutation inducing cancer after transplantation, as well as low risk of tumorigenicity due to contamination of undifferentiated cells.

Construction of a foundation for stably supplying iPS cells to customers while maintaining and ensuring the quality of iPS cells is a future problem.

It is preferable to construct a management system capable of accurately bi-directionally searching for massive amounts and a wide variety of various data such as the data (sexes, ages, medical histories, health conditions, genetic backgrounds, and the like) of donors themselves, the data of acceptance of somatic cells as ingredients for generating iPS cells, the results of quality tests for generated iPS cells, and additional production and stock states.

Thus, it is demanded to construct a system for stably supplying high-quality iPS cells to a customer under accurate quality management.

A first aspect of the present invention is to provide a system for an iPS cell bank including: a terminal apparatus that receives a request to produce an iPS cell from a customer; and a server apparatus that manages a step of accepting a somatic cell including a blood cell, a skin cell, or the like as an ingredient for producing the iPS cell (hereinafter referred to as "somatic cell"), a step of producing the iPS cell, a step of stocking the produced iPS cell, and a step of transporting the produced iPS cell, wherein the terminal apparatus includes: an entry unit that makes an entry of the production request, including a desired date of collection of the somatic cell, from the customer, as well as customer identification information for identifying the customer; and a terminal sending unit that sends the entered production request and the entered customer identification information to the server apparatus; and wherein the server apparatus includes: a storage unit that stores a collectable date on which the somatic cell can be collected, a producible period during which the iPS cell can be produced, and a stockable location and a stockable period where the produced iPS cell can be stocked; a receiving unit that receives the sent production request and the sent customer identification information; a determination unit that determines: a date of collection of the somatic cell based on the desired collection date included in the received production request and on the stored collectable date; a period of production of the iPS cell based on the determined date of collection of the somatic cell and on the stored producible period; a date of acceptance of the somatic cell based on the determined date of collection of the somatic cell and on the determined production period; a stock location and a stock period for stocking the produced iPS cell based on the determined production period and on the stored stockable location and stockable period; and a date of shipment of the produced iPS cell based on the determined production period, the determined stock location, and the determined stock period; a storage processing unit that stores, in the storage unit, the determined date of collection of the somatic cell, the determined production period, the determined date of acceptance of the somatic cell, the determined stock location, the determined stock period, and the determined date of shipment of the iPS cell in association with the received customer identification information; and a server sending unit that sends the date of collection of the somatic cell, the production period, the date of acceptance of the somatic cell, the stock location, the stock period, and the date of shipment of the iPS cell, stored in association with the customer identification information, to the customer represented by the stored customer identification information.

A second aspect of the present invention is to provide the system for the iPS cell bank according to the first aspect, wherein the somatic cell is a blood cell.

A third aspect of the present invention is to provide a method executed in a system for an iPS cell bank including: a terminal apparatus that receives a request to produce an iPS cell from a customer; and a server apparatus that manages a step of accepting a somatic cell for producing the iPS cell, a step of producing the iPS cell, a step of stocking the produced iPS cell, and a step of transporting the produced iPS cell, the method executed in the terminal apparatus includes: a step of making an entry of the production request, including a desired date of collection of the somatic cell, from the customer, as well as customer identification information for identifying the customer; and a step of sending the entered production request and the entered customer identification information to the server apparatus; and the method executed in the server apparatus includes: a step of storing a collectable date on which the somatic cell can be collected, a producible period during which the iPS cell can be produced, and a stockable location and a stockable period where the produced iPS cell can be stocked; a step of receiving the sent production request and the sent customer identification information; a step of determining a date of collection of the somatic cell based on the desired collection date included in the received production request and on the stored collectable date; a step of determining a period of production of the iPS cell based on the determined date of collection of the somatic cell and on the stored producible period; a step of determining a date of acceptance of the somatic cell based on the determined date of collection of the somatic cell and on the determined production period; a step of determining a stock location and a stock period for stocking the produced iPS cell based on the determined production period and on the stored stockable location and stockable period; a step of determining a date of shipment of the iPS cell based on the determined production period, the determined stock location, and the determined stock period; a step of storing, in the storage unit, the determined date of collection of the somatic cell, the determined production period, the determined date of acceptance of the somatic cell, the determined stock location, the determined stock period, and the determined date of shipment of the iPS cell in association with the received customer identification information; and a step of sending the date of collection of the somatic cell, the production period, the date of acceptance of the somatic cell, the stock location, the stock period, and the date of shipment of the iPS cell, stored in association with the customer identification information, to the customer represented by the stored customer identification information.

According to one aspect of the present invention, each step is managed in consideration of the quality of a somatic cell which is an ingredient and an iPS cell to be a product, and therefore, a high-quality iPS cell can be efficiently and stably supplied to a customer as needed.

BRIEF DESCRIPTION OF THE DRAWINGS

FIG. 3 is a schematic view representing the table structure of a database (DB) according to the embodiment; and FIG. 4 is a sequence diagram representing the operation of the system for the iPS cell bank according to the embodiment.

DETAILED DESCRIPTION

Figure 1:
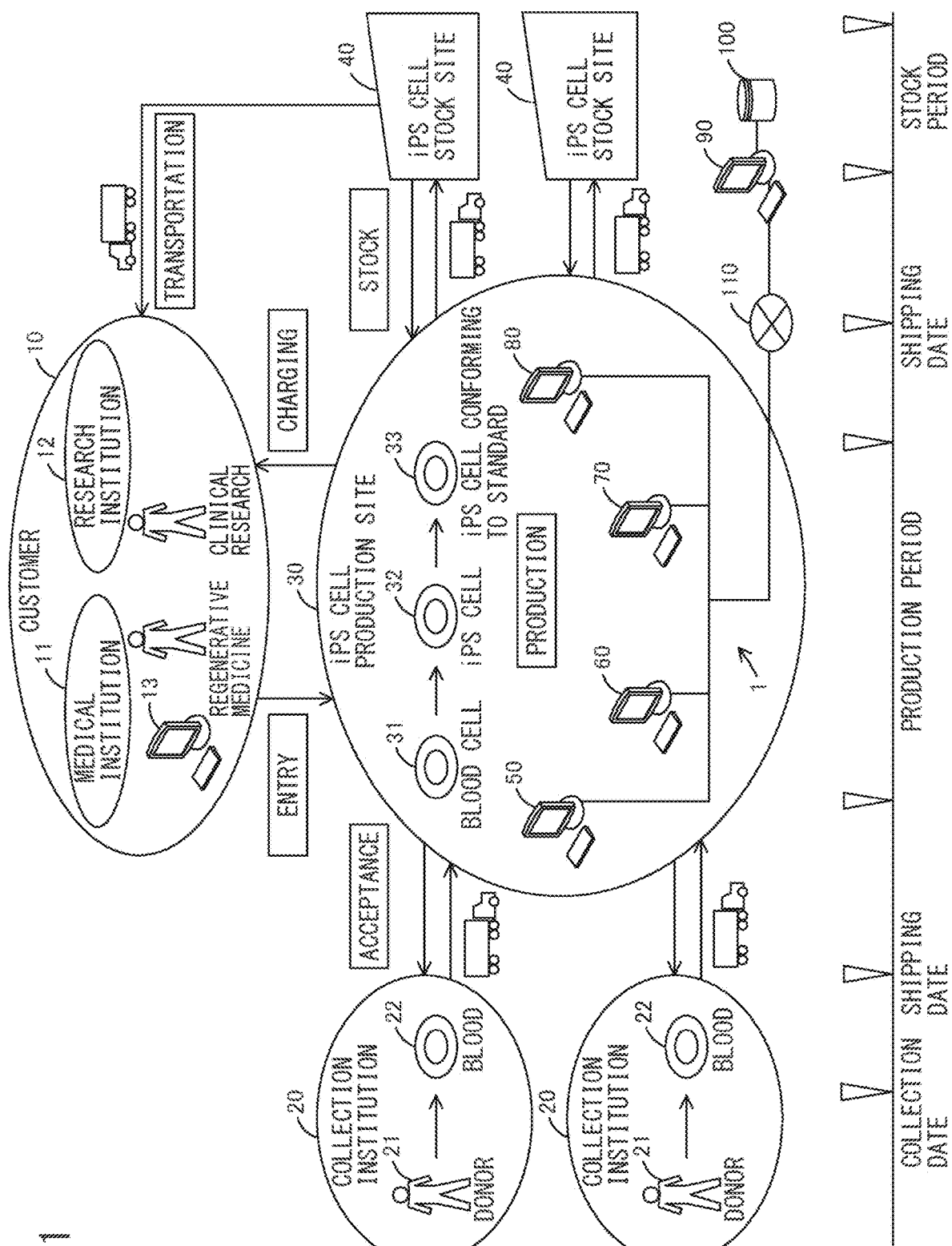
FIG. 1 is a schematic view illustrating a business model and a system for an iPS cell bank according to one embodiment of the present invention.

Embodiments of the present invention will be described in detail below with reference to the accompanying drawings. In each drawing, similar components are denoted by similar reference characters. The technical scope of the invention and the significance of terms described in Claims are not limited by contents described below.

(Summary of Business Model)

First, the summary of a business model according to the present invention will be described with reference to FIG. 1. FIG. 1 is a schematic view illustrating a business model and a system for an iPS cell bank according to an embodiment. The business model is a business model in which an iPS cell production site 30 receives a request to produce an iPS cell from a customer 10, accepts a somatic cell such as a blood cell from a collection institution 20, generates an iPS cell 32 from the accepted somatic cell, and evaluates the quality of the generated iPS cell 32, followed by stocking an iPS cell 33 conforming to a predetermined standard to an iPS cell stock site 40 and by transporting the iPS cell 33, by a transporting vehicle or aircraft, to the customer 10 depending on demand and charging the customer 10.

Examples of the collection institution 20 include a hospital, a blood donation site, and another collection institution in which blood 22 which is a somatic cell can be collected from a donor 21 such as a patient. Such collection institutions 20 are established in plural bases (for example, Tokyo, Osaka, Fukuoka, and the like). The collection institution 20 collects the blood 22 from the donor 21 on a collection date of which notification is provided from the iPS cell production site 30, and ships the collected blood 22 on a shipping date of which notification is provided from the iPS cell production site 30. The shipped blood 22 is transported, by a transporting vehicle or aircraft, to the iPS cell production site 30 in the state of appropriately managing the temperature of the blood.

Examples of the iPS cell production site 30 include a medical institution, a research institution, and another production institution in which the iPS cell 33 can be produced. The iPS cell production site 30 notifies the collection institution 20 of a collection date and an acceptance date automatically determined by a system 1 for an iPS cell bank to accept a somatic cell when making an entry of a production request from the customer 10. In such a manner, the collected blood is transported, by a transporting vehicle or aircraft, to the iPS cell production site 30.

The iPS cell production site 30 produces the iPS cell 33 within a production period automatically determined by the system 1 for the iPS cell bank. The iPS cell production site 30 introduces an inducer into a collected blood cell 31 which is a somatic cell to generate the iPS cell 32, and conducts a test of the quality of the generated iPS cell 32 (differentiation-inducing property testing, gene mutation testing, fungal, bacterial, and viral testing, and the like) to produce the iPS cell 33 conforming to the standard. The iPS cell production site 30 ships the iPS cell 33 to a stock location automatically determined by the system 1 for the iPS cell bank, on a shipping date automatically determined by the system 1 for the iPS cell bank. The shipped iPS cell 33 is transported, by a transporting vehicle or aircraft, to the iPS cell stock site 40 in the state of appropriately managing the temperature of the iPS cell 33.

Examples of the iPS cell stock site 40 include a warehouse, a medical institution, and another stock site in which the iPS cell 33 can be stocked. Such iPS cell stock sites 40 are established in plural bases (for example, Tokyo, Osaka, Fukuoka, and the like). The iPS cell stock site 40 cryopreserves the iPS cell 33 and regularly conducts thawing testing during a stock period automatically determined by the system 1 for the iPS cell bank, as well as carries out reconfirmation when the iPS cell 33 is used. The iPS cell stock site 40 transports the stocked iPS cell 33 to the customer 10 depending on demand. The transported iPS cell 33 is transported, by a transporting vehicle or aircraft, to the customer 10 in the state of appropriately managing the temperature of the iPS cell 33.

(Configuration of System for iPS Cell Bank)

The configuration of the system for the iPS cell bank will now be described with reference to FIG. 1. The system 1 for the iPS cell bank manages an entry step of receiving a request to produce an iPS cell from a customer, an acceptance step of accepting the somatic cell 31, a production step of producing the iPS cell 33, a stock step of stocking the iPS cell 33, and a transportation step of transporting the iPS cell 33, by a transporting vehicle or aircraft, to the customer. The system 1 for the iPS cell bank is a cloud computing system having a three-level architecture including terminal apparatuses 50 to 80 and a server apparatus 90. The terminal apparatuses 50 to 80 and the server apparatus 90 are interconnected through a network 110.

The terminal apparatuses 50 to 80 include a PC, a tablet PC, and another computer apparatus. The terminal apparatuses 50 to 80 include the entry management terminal 50 for managing the entry step, the acceptance management terminal 60 for managing the acceptance step, the production process management terminal 70 for managing the production step, and the stock management terminal 80 for managing the stock step. The terminal apparatuses 50 to 80 are configured to send the management information of each step to the server apparatus 90 and to receive the management information from the server apparatus 90.

The server apparatus 90 includes a workstation and another computer apparatus. The server apparatus 90 has a DB 100 in which the management information of all the steps is stored, and the DB 100 has a relational database management system (RDBMS). The server apparatus 90 is configured to receive the management information of each step from the terminal apparatuses 50 to 80 to store the management information in the DB 100, and to read the management information from the DB 100 to send the management information to the terminal apparatuses 50 to 80.

(Configurations of Terminal Apparatuses and Server Apparatus)

Figure 2:
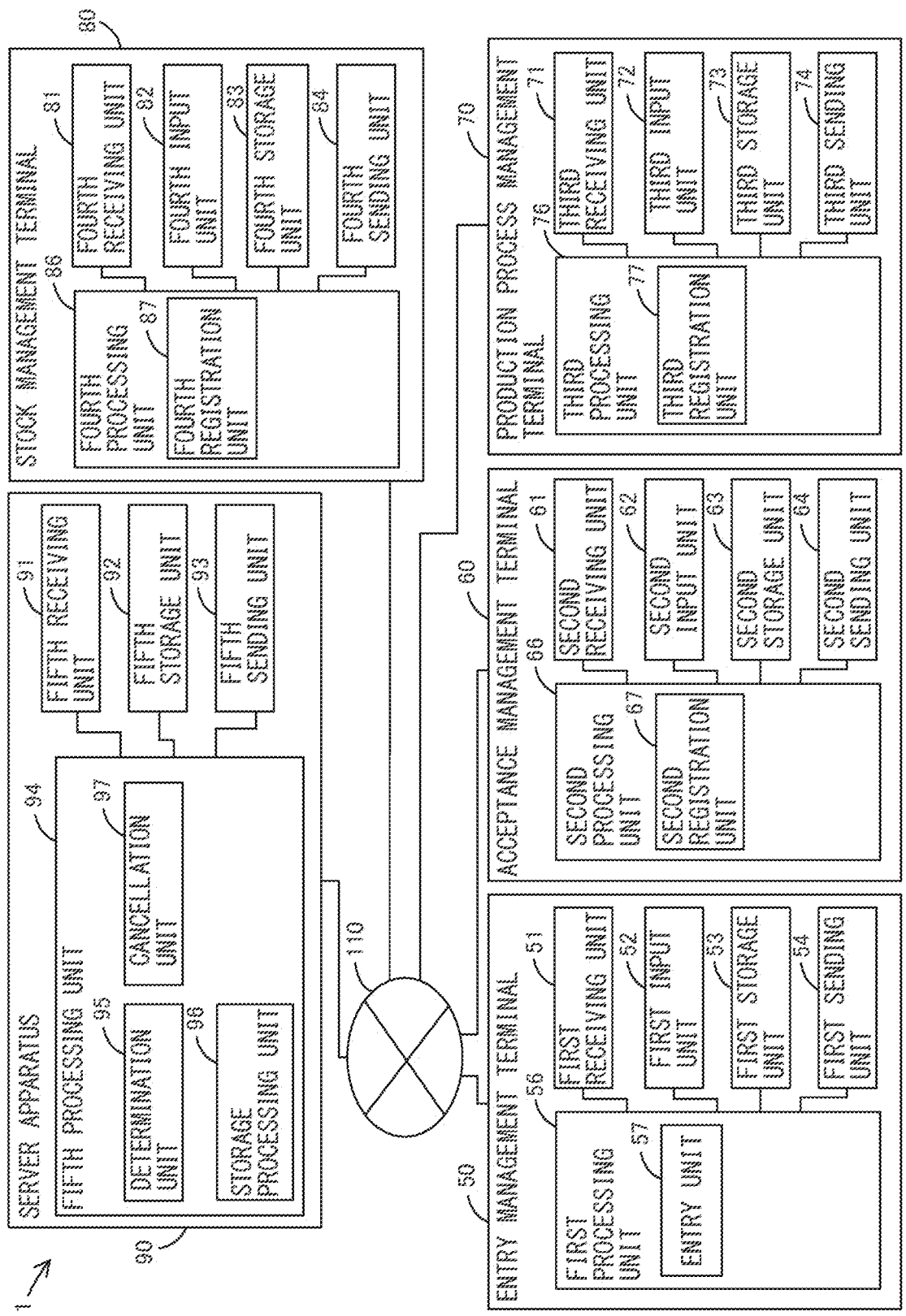
FIG. 2 is a block diagram illustrating terminal apparatuses and a server apparatus according to the embodiment.

The configurations of the terminal apparatuses and the server apparatus will now be described in more detail with reference to FIG. 2. FIG. 2 is a block diagram illustrating the terminal apparatuses and the server apparatuses according to the embodiment.

The entry management terminal 50 includes: a first receiving unit 51 that receives information through the network 110; a first input unit 52 including a keyboard, a mouse, a scanner, and other input means; a first storage unit 53 including a hard disk drive (HDD), a solid state drive (SSD), and other nonvolatile storage means; a first sending unit 54 that sends information through a network 55; a first processing unit 56 including a central processing unit (CPU) and other processing means; and an entry unit 57 including a user interface (UI) program in a presentation layer.

The entry unit 57 provides an entry screen for making an entry of a production request from a customer, including a desired date of collection of a somatic cell as well as a desired location for stocking an iPS cell and a desired period of stock of the iPS cell as needed, as well as a customer ID for identifying the customer.

Simultaneously, for example, the actual measurement values and the provisional values of visual inspection, microscopic inspection, collection yield, a survival rate, cell characteristic analysis, microorganism testing, and the like are recorded and presented as acceptance inspection items for collected somatic cells.

The first sending unit 54 sends the entered production request and customer ID to the server apparatus 90.

The acceptance management terminal 60 includes: a second receiving unit 61 that receives information through the network 110; a second input unit 62 including a keyboard, a mouse, a scanner, and other input means; a second storage unit 63 including an HDD, an SSD, and other nonvolatile storage means; a second sending unit 64 that sends information through the network 110; a second processing unit 66 including a CPU and other processing means; and a second registration unit 67 including a UI program in a presentation layer.

The second registration unit 67 provides a registration screen for registering collectable dates on which somatic cells can be collected, which are obtained from plural collection institutions, as well as collection institution IDs for identifying the collection institutions.

The second sending unit 64 sends the registered collectable dates and the collection institution IDs to the server apparatus 90.

The production process management terminal 70 includes: a third receiving unit 71a that receives information through the network 110; a third input unit 72 including a keyboard, a mouse, a scanner, and other input means; a third storage unit 73 including an HDD, an SSD, and other nonvolatile storage means; a third sending unit 74 that sends information through the network 110; a third processing unit 76 including a CPU and other processing means; and a third registration unit 77 including a UI program in a presentation layer.

The third registration unit 77 provides a registration screen for registering a producible period during which an iPS cell can be produced, and the quality test result of the iPS cell.

The third sending unit 74 sends the registered producible period to the server apparatus 90.

The stock management terminal 80 includes: a fourth receiving unit 81 that receives information through the network 110; a fourth input unit 82 including a keyboard, a mouse, a scanner, and other input means; a fourth storage unit 83 including an HDD, an SSD, and other nonvolatile storage means; a fourth sending unit 84 that sends information through the network 110; a fourth processing unit 86 including a CPU and other processing means; and a fourth registration unit 87 including a UI program in a presentation layer.

The fourth registration unit 87 provides a registration screen for registering stockable locations and stockable periods obtained from plural iPS cell stock sites, as well as stock site IDs for identifying the iPS cell stock sites.

The fourth sending unit 84 sends the registered stockable locations, stockable periods, and stock site IDs to the server apparatus 90.

The server apparatus 90 includes: a fifth receiving unit 91 that receives information through the network 110; a fifth storage unit 92 including an HDD, an SSD, and other nonvolatile storage means; a fifth sending unit 93 that sends information through the network 110; a fifth processing unit 94 including a CPU and other processing means; a determination unit 95 including a business logic (BL) program in an application layer; a storage processing unit 96 including a DB program in a data layer; and a cancellation unit 97 including a BL program.

The storage processing unit 96 stores, in the fifth storage unit 92, the collectable date on which a somatic cell can be collected, the producible period during which an iPS cell can be produced, and the stockable location and the stockable period where the iPS cell can be stocked, sent from the terminal apparatuses 50 to 80.

The fifth receiving unit 91 receives the production request and the customer ID sent from the entry management terminal 50.

The determination unit 95 determines a date of collection of the somatic cell based on the desired collection date included in the sent production request and on the stored collectable date.

The determination unit 95 determines a period of production of the iPS cell based on the determined date of collection of the somatic cell and on the stored producible period during which the iPS cell can be produced.

The determination unit 95 determines a date of acceptance of the somatic cell based on the determined date of collection of the somatic cell and on the determined production period.

The determination unit 95 determines a stock location and a stock period where the iPS cell is stocked based on the determined period of production of the iPS cell and on the stored stockable location and stockable period where the iPS cell can be stocked.

The determination unit 95 determines a date of shipment of the iPS cell based on the determined production period and on the determined stock location and stock period.

The cancellation unit 97 cancels the determined shipment of the iPS cell when the registered quality test result of the iPS cell is inadequate.

The storage processing unit 96 stores, in the fifth storage unit 92, the determined collection date, production period, date of acceptance of blood which is the somatic cell, stock location and stock period where the iPS cell is stocked, and date of shipment of the iPS cell, in association with a customer ID.

The fifth sending unit 93 sends the date of collection of the somatic cell, the production period, the date of acceptance of the somatic cell, the stock location and stock period where the iPS cell is stocked, and the date of shipment of the iPS cell, stored in association with the customer ID, to the customer indicated by the customer ID.

(Table Structure of DB)

The table structure of a DB will now be described with reference to FIG. 3. FIG. 3 is a schematic view representing the table structure of the DB according to the embodiment. The DB includes an entry table 101 in which a production request is stored, an acceptance table 102 in which acceptance information is stored, a production process table 103 in which production step information is stored, and a stock table 104 in which stock information is stored.

The entry table 101 includes an entry ID, an entry date, a customer ID, and first, second, and third desired collection dates for a somatic cell.

The acceptance table 102 includes an acceptance ID, a collection institution ID, a collectable date on which a somatic cell can be collected, an entry ID, a date of collection of blood, and a date of shipment of blood.

The production process table 103 includes a production ID, a producible period during which an iPS cell can be produced, an entry ID, a period of production of an iPS cell, and a date of shipment of an iPS cell.

The stock table 104 includes a stock ID, a stock site ID, a stockable location where an iPS cell can be stocked, a stockable period during which an iPS cell can be stocked, an entry ID, a stock location of stocking an iPS cell, and a stock period of stocking an iPS cell.

(Operation of System for iPS Cell Bank)

The operation of the system for iPS cell bank will now be described with reference to FIG. 4. FIG. 4 is a sequence diagram representing the operation of the system for the iPS cell bank according to the embodiment. Step S100 to step S106 may be carried out in any processing order.

In step S100, an acceptance management terminal sends collectable dates, obtained from plural collection institutions, as well as collection institution IDs to a server apparatus. Then, in step S101, the server apparatus stores, in an entry table, the received collectable dates, as well as acceptance IDs and the collection institution IDs.

In step S102, a production process management terminal sends, to the server apparatus, a producible period during which an iPS cell can be produced. Then, in step S103, the server apparatus stores, in a production process table, the received producible period during which the iPS cell can be produced, as well as a production ID.

In step S104, a stock management terminal sends, to the server apparatus, stockable locations and stockable periods obtained from plural iPS cell stock sites. Then, in step S105, the server apparatus stores, in a stock table, the received stockable locations and stockable periods, as well as stock IDs and stock site IDs.

In step S106, an entry management terminal receives a production request including first to third desired collection dates from a customer, as well as a customer ID. Then, in step S107, the entry management terminal sends, to the server apparatus, the received production request including the first to third desired collection dates, as well as the customer ID.

Subsequently, in step S108, the server apparatus determines a date of collection of a somatic cell based on the first to third desired collection dates included in the received production request and on the stored collectable dates.

The processing of step S108 will now be described in detail with reference to FIG. 3. The server apparatus extracts, from the acceptance table 102, a collectable date of a collection institution matching the first desired collection date (2018 Mar. 15) of a donor for an entry ID (0001). Because the collectable date matching the first desired collection date (2018 Mar. 15) does not exist in the acceptance table 102, the server apparatus extracts, from the acceptance table 102, a collectable date of a collection institution matching the second desired collection date (2018 Mar. 16) of the donor. Because the collectable date (2018 Mar. 16) matching the second desired collection date (2018 Mar. 16) exists in the acceptance table 102, the server apparatus determines the collectable date (2018 Mar. 16) as a collection date. When any collectable dates matching first to third desired collection dates do not exist in the acceptance table, the server apparatus provides notification of resetting of desired collection dates.

Referring to FIG. 4, subsequently, in step S109, the server apparatus determines a production period for producing an iPS cell based on the determined date of collection of the somatic cell and on the stored producible period during which the iPS cell can be produced.

The processing of step S109 will be described in more detail with reference to FIG. 3. For the entry ID (0001), the server apparatus adds a time of transportation of a somatic cell determined depending on a collection institution (for example, 1 day in the Tokyo collection site) to the determined collection date (2018 Mar. 16) to determine an earliest delivery date on which the somatic cell is delivered to the iPS cell production site earliest (2018 Mar. 17), and adds a quality preservable period during which the quality of the collected somatic cell can be preserved (for example, 2 days in the case of blood) to determine a latest delivery date on which the somatic cell is delivered to an iPS cell production site latest (2018 Mar. 18), whereby a deliverable period during which the somatic cell can be delivered from the collection institution to the iPS cell production site (2018 Mar. 17 to 2018 Mar. 18) is calculated. Then, the server apparatus extracts, from the production process table 103, the earliest producible period (2018 Mar. 16 to 2018 Sep. 16) of producible periods (2018 Mar. 16 to 2018 Sep. 16, and 2018 Mar. 17 to 2018 Sep. 17) overlapping with the calculated deliverable period (2018 Mar. 17 to 2018 Mar. 18), and determines a production period during which an iPS cell is produced (2018 Mar. 16 to 2018 Sep. 16). As a result, a period of production of an iPS cell is determined in consideration of the quality of a somatic cell, and therefore, a high-quality iPS cell can be stably supplied to a customer. "Production period" in this example means a period from the acceptance of a somatic cell in an iPS cell production site to the completion of the evaluation of the quality of an iPS cell, and includes not only a substantial period of generation of the iPS cell (3 months) but also a period of evaluation of the quality of the generated iPS cell (3 months).

Referring to FIG. 4, in step S110, the server apparatus then determines an acceptance date on which the collected somatic cell is accepted in the iPS cell production site based on the determined date of collection of the somatic cell and on the determined period of production of the iPS cell.

The processing of step S110 will be described in more detail with reference to FIG. 3. For the entry ID (0001), the server apparatus adds a time of transportation of the somatic cell (for example, 1 day in the Tokyo collection site) determined depending on a collection institution to the determined date of collection of the somatic cell (2018 Mar. 16) to determine an acceptance date (2018 Mar. 17), checks that the determined acceptance date (2018 Mar. 17) is within the period of production of the iPS cell (2018 Mar. 16 to 2018 Sep. 16), and determines a date of acceptance of the somatic cell (2018 Mar. 17).

Referring to FIG. 4, in step S111, the server apparatus then determines a stock location and a stock period where the iPS cell is stocked based on the determined period of production of the iPS cell and on the stored stockable location and stockable period.

The processing of step S111 will be described in more detail with reference to FIG. 3. For the entry ID (0001), the server apparatus adds a time of transportation of an iPS cell (for example, 1 day in the Tokyo stock site) determined depending on an iPS cell stock site to the date of the completion of the determined production period (2018 Sep. 16) to determine an earliest delivery date on which the iPS cell is delivered to the iPS cell stock site earliest (2018 Sep. 17), and adds a quality assurance period during which the quality of the produced iPS cell can be ensured (for example, 4 days in the case of preservation in liquid nitrogen) to determine a latest delivery date on which the iPS cell is delivered to the iPS cell production site latest (2018 Sep. 20), whereby a deliverable period during which the iPS cell can be delivered from the iPS cell production site to the iPS cell stock site (2018 Sep. 17 to 2018 Sep. 20) is calculated. Then, the server apparatus extracts, from the stock table 104, a stockable period (2018 Sep. 19 to 2068 Sep. 19) which is the earliest stockable period (2018 Sep. 19-2068 Sep. 19) of stockable periods (2018 Sep. 19 to 2068 Sep. 19, and 2018 Sep. 20 to 2068 Sep. 20) overlapping with the calculated deliverable period (2018 Sep. 17 to 2018 Sep. 20), and determines a stock period (2018 Sep. 19-2068 Sep. 19) and a stock location (for example, Tokyo stock site) where an iPS cell is stocked. As a result, a stock location and a stock period are determined in consideration of the quality of an iPS cell, and therefore, a high-quality iPS cell can be stably supplied to a customer.

Referring to FIG. 4, in step S112, the server apparatus then determines a date of shipment of the produced iPS cell based on the determined period of production of the iPS cell and on the determined stock location and stock period.

The processing of step S112 will now be described in detail with reference to FIG. 3. For the entry ID (0001), the server apparatus subtracts a time of transportation of an iPS cell determined depending on an iPS cell stock site (for example, 1 day in the Tokyo stock site) from the starting date (2018 Sep. 19) of the determined stock period to determine a shipping date (2018 Sep. 18), checks that the determined shipping date (2018 Sep. 18) is after the date of the completion of the production period (2018 Sep. 16), and determines a date of shipment of the iPS cell (2018 Sep. 18).

Referring to FIG. 4, subsequently, in step S113, the server apparatus stores the determined information, i.e., the determined collection date, production period, date of acceptance of the somatic cell, stock location and stock period, and date of shipment of the iPS cell, in association with the customer ID.

In step S114, the server apparatus sends the determined information, i.e., the determined collection date, production period, date of acceptance of the somatic cell, stock location and stock period, and date of shipment of the iPS cell, to the customer indicated by the customer ID.

Following step S114, the server apparatus includes a step of registering the quality test result of the iPS cell, and a step of canceling the determined shipment of the iPS cell as represented in FIG. 3 when the registered quality test result of the iPS cell is inadequate.

The operation-effect of the system for the iPS cell bank of the embodiment will now be described. A high-quality iPS cell can be stably supplied to a customer because the server apparatus determines a period of production of an iPS cell in consideration of the quality preservable period of a somatic cell (for example, 2 days in the case of blood) as described in the processing of step S109.

A high-quality iPS cell can be stably supplied to a customer because the server apparatus determines a stock location and a stock period where an iPS cell is stocked in consideration of the quality assurance period (for example, 4 days in the case of preservation in liquid nitrogen) of an iPS cell conforming to a quality test as described in the processing of step S111.

All of the programs according to the embodiment are recorded on a computer-readable non-transitory recording medium, for example, CD-ROM, and thus provided.

The various embodiments have been described in the present specification. However, it should be understood that the present invention is not limited to the various embodiments described above, and various modifications can be made within the scope described in the following claims.

The invention claimed is:

1. A cell production management system for managing a production from a somatic cell to a target cell, the system comprising:
   a terminal apparatus and a server apparatus that are connected communicably to each other; and
   a transporting apparatus that transports the somatic cell or the target cell,
   wherein the terminal apparatus comprises:
      a first processor that controls transmitting data to the server apparatus, the data including a desired date of collection of the somatic cell, a collectable date on which the somatic cell can be collected, and a producible period during which the target cell can be produced,
   wherein the server apparatus comprises:
      a second processor that
         controls receiving data from the terminal apparatus, the data including the desired date of collection, the collectable date, the producible period, and
         determines a collection date of the somatic cell, a production period of the target cell, and an acceptance date of the somatic cell, based on the desired date of collection, the collectable date, and the producible period, and
   wherein the transporting apparatus transports the somatic cell collected on the collection date determined by the second processor so that the somatic cell is accepted on the acceptance date determined by the second processor.

2. The cell production management system according to claim 1,
   wherein the first processor controls transmitting data to the server apparatus, the data including a stockable location and a stockable period where the produced target cell can be stocked,
   wherein the second processor
      controls receiving data from the terminal apparatus, the data including the stockable location and the stockable period, and
      determines a stock location and a stock period of the produced target cell and a shipping date of the produced target cell, based on the production period, the stockable location and the stockable period, and
   wherein the transporting apparatus transports the target cell produced during the production period so that the target cell is shipped on the shipping date.

3. The cell production management system according to claim 2, wherein the transporting apparatus transports the target cell stocked at the stock location during the stock period.

4. The cell production management system according to claim 1, wherein the second processor
   adds a time of transportation of the somatic cell to the determined collection date of the somatic cell to determine an earliest delivery date on which the somatic cell is delivered to a cell production site earliest, and adds a quality preservable period during which the quality of the somatic cell can be preserved, to the determined collection date of the somatic cell to determine a latest delivery date on which the somatic cell is delivered to the cell production site latest, whereby a deliverable period between the earliest delivery date and the latest delivery date is calculated, and
   determines the production period of the target cell based on an earliest producible period of the producible periods overlapping with the calculated deliverable period.

5. The cell production management system according to claim 1, wherein the second processor
   adds a time of transportation of the somatic cell to the determined collection date of the somatic cell to determine the acceptance date of the somatic cell,
   checks that the determined acceptance date is within the production period of the target cell, and
   determines the acceptance date of the somatic cell.

6. The cell production management system according to claim 1, wherein the second processor
   adds a time of transportation of the target cell to a completion date of the production to determine an earliest delivery date on which the target cell is delivered to a cell stock site earliest, and adds a quality assurance period during which the quality of the produced target cell can be ensured, to the completion date of the production to determine a latest delivery date on which the target cell is delivered to the cell production site latest, whereby a deliverable period between the earliest delivery date and the latest delivery date is calculated, and
   determines a stock period and a stock location where the target cell is stocked based on an earliest stockable period of the stockable periods overlapping with the calculated deliverable period.

7. The cell production management system according to claim 6, wherein the second processor
   subtracts the time of transportation of the target cell from a starting date of the stock period to determine a shipping date of the produced target cell,
   checks that the determined shipping date is after the completion date of the production period, and
   determines the shipping date of the target cell.

\* \* \* \* \*